(12) United States Patent
Girgis

(10) Patent No.: US 11,648,354 B2
(45) Date of Patent: May 16, 2023

(54) PEEL-OFF PACKAGING FOR PEN NEEDLES AND SYRINGE NEEDLES

(71) Applicant: Embecta Corp., Andover, MA (US)

(72) Inventor: Peter A. Girgis, Franklin Lakes, NJ (US)

(73) Assignee: Embecta Corp., Andover, MA (US)

(*) Notice: Subject to any disclaimer, the term of this patent is extended or adjusted under 35 U.S.C. 154(b) by 198 days.

(21) Appl. No.: 17/066,344

(22) Filed: Oct. 8, 2020

(65) Prior Publication Data

US 2022/0111151 A1    Apr. 14, 2022

(51) Int. Cl.
*A61M 5/32*    (2006.01)
*A61M 5/31*    (2006.01)

(52) U.S. Cl.
CPC ..... *A61M 5/3202* (2013.01); *A61M 2005/311* (2013.01); *A61M 2005/312* (2013.01)

(58) Field of Classification Search
CPC .. A61M 5/3202; A61M 5/002; A61M 5/3205; A61M 2005/311; A61M 2005/312; A61M 2209/06
See application file for complete search history.

(56) References Cited

U.S. PATENT DOCUMENTS

| | | | |
|---|---|---|---|
| 8,944,245 B2 | 2/2015 | Erickson et al. | |
| 10,213,589 B2 | 2/2019 | Solomon et al. | |
| 10,391,295 B2 | 8/2019 | Ryan et al. | |
| 2012/0216359 A1* | 8/2012 | Rogers | B08B 1/00 15/104.93 |
| 2017/0349315 A1* | 12/2017 | Yang | A61M 5/002 |
| 2019/0038888 A1 | 2/2019 | Gardner | |
| 2020/0331687 A1* | 10/2020 | Horvath | A61M 5/3205 |

* cited by examiner

*Primary Examiner* — Tasnim Mehjabin Ahmed
(74) *Attorney, Agent, or Firm* — Greenberg Traurig, LLP; David J. Dykeman; Roman Fayerberg

(57) ABSTRACT

A multiple pen needle or syringe needle storage and dispensing system where a plurality of needle devices such as pen needles including a cover can be disposed on strip, where the strip serves a seal for multiple needle devices. Each needle device can be peeled off the strip unsealed for immediate use for example in an injections device, or separated from the strip sealed for later use.

19 Claims, 4 Drawing Sheets

CONVENTIONAL
FIG.1A
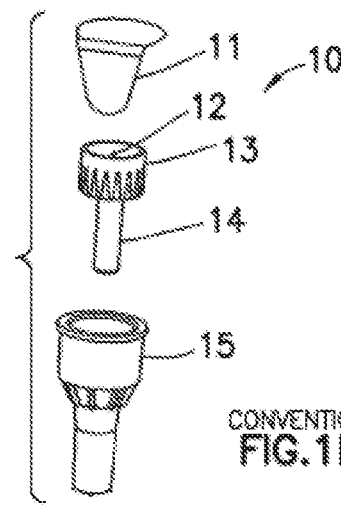
CONVENTIONAL
FIG.1B
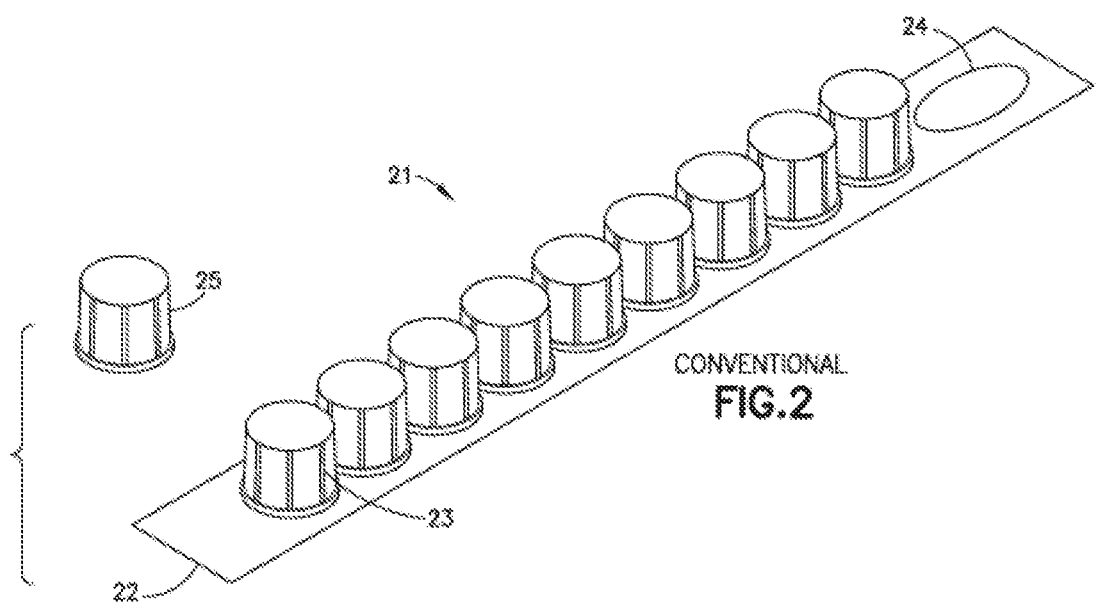
CONVENTIONAL
FIG.2

PEEL-OFF PACKAGING FOR PEN NEEDLES AND SYRINGE NEEDLES

FIELD OF THE DISCLOSURE

Generally, exemplary embodiments of the present disclosure relate to the fields of pen needles and syringe needles, and in particular to packaging and storage of pen needles and syringe needles.

BACKGROUND OF THE DISCLOSURE

Conventionally, as illustrated in FIGS. 1A and 1B, pen needles 10 include a hub 13 receiving a needle 12 with an inner shield 14 connected to the hub and covering the patient end of the needle. Pen needle 10 are provided with an outer cover 15 covering the inner shield and hub and a seal 11 covering the non-patient needle end of the hub. That is, pen needles 10 are packaged individually with a tear drop label or seal 11 on the back of each outer cover 15 acting as a sterility barrier. Conventionally, syringe needles are also packaged individually in a blister pack for sterility.

There are pen needle storage systems, such as those disclosed in U.S. Pat. No. 10,745,188 the entire disclosure of which is incorporated herein by reference, where individually packaged pen needles can be connected to each other via connecting members.

On the other hand, there are other products, such as the disinfecting caps disclosed in U.S. Pat. No. 10,391,295 the entire disclosure of which is incorporated herein by reference, utilize a conventional foil strip system 21 as illustrated in FIG. 2, where a plurality of disinfection caps 23 can be disposed on a strip 22, which includes an opening 24, for example for hanging strip 22 on an IV pole. Strip 22 can serve as a common lid for caps 23 disposed thereon, such that removed cap 25 is ready for immediate use.

However, there are no systems designed specifically for pen needles or syringe needles that provide convenient packaging for storage of multiple pen needles or syringe needles while allowing convenient retrieval of one or more pen needles of syringe needles for immediate or later use.

SUMMARY OF THE DISCLOSURE

In accordance with exemplary aspects of the present disclosure, system for storing and dispensing needles comprises a plurality of needle devices each including a needle and an outer cover covering the needle, and a strip attached to the outer cover of each needle devices provides a common seal for the outer cover of each the needle devices. Each of the needle devices is configured to be individually removable from the strip, and removal of the needle device from the strip detaches the strip from the outer cover of the removed needle device and exposes the needle of the removed needle device for immediate use.

In accordance with another aspect of the present disclosure, the strip comprises a plurality of portions separated by at least one perforation between these portions such that one of the needle devices can be attached to one of the portions of said strip, and another of the needle devices can be attached to another portion of the strip separated by the perforation.

In accordance with yet another aspect of the present disclosure, when least one the needle devices is detached from the strip, a portion of said strip can be detached from the strip at the perforation and the needle devices can remains attached to the detached portion of the strip.

In accordance with still further aspect of the present disclosure, the strip can include a first side and an opposing second side, such that first and second needle devices can be sealingly attached to the first side, and third and fourth needle devices can be sealingly attached to the second side.

Exemplary implementations of the disclosed embodiments can achieve potential cost savings on current manufacturing steps and materials used by disposing multiple pen needles or syringe needles on a single peel-off strip.

Exemplary implementations of the disclosed embodiments can provide patients with an easy to use peel-off solution that can overcome potential struggles some patients may currently experience with the removal of conventional tear-drop labels.

Exemplary implementations of the disclosed embodiments can allow users to tear off as many pen needle or syringe needle units as they need, whether they're at home or on the go, potentially saving the user multiple trips to a container storing individually packaged needles.

Exemplary implementations of the disclosed embodiments may can provides a unique packaging over other pen needle and syringe needle products.

Exemplary implementations of the disclosed embodiments may can facilitate a more organized layering of multiple pen needle and syringe needle within containers.

Objects, advantages, and salient features of the disclosure become apparent from the following detailed description, which, taken in conjunction with the annexed drawings, discloses exemplary embodiments of the disclosure.

BRIEF DESCRIPTION OF THE DRAWINGS

The above benefits and other advantages of the various embodiments of the present disclosure will be more apparent from the following detailed description of exemplary embodiments of the present disclosure and from the accompanying drawing figures, in which:

FIGS. 1A and 1B are three-dimensional views of a conventional pen needle, and its components and packaging.

FIG. 2 is an illustration of a conventional device for hanging caps on an IV pole.

Throughout the drawings, like reference numbers will be understood to refer to like parts, components and structures.

DETAILED DESCRIPTION OF THE EXEMPLARY EMBODIMENTS

Figure 3A:
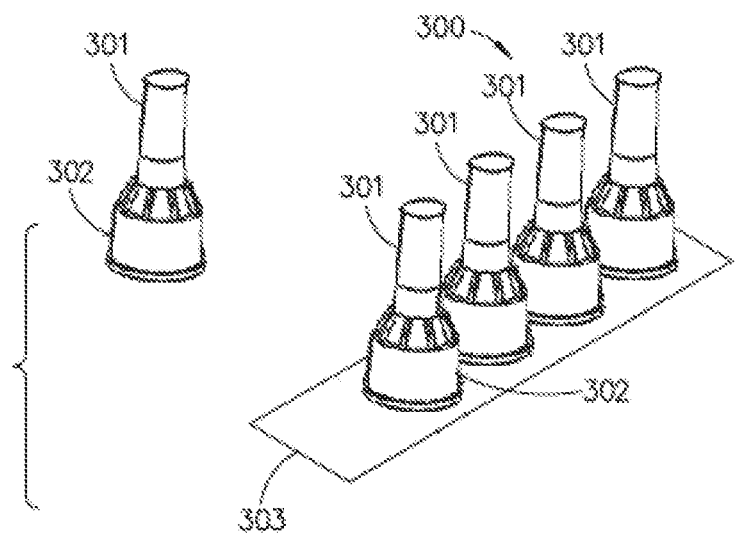
FIGS. 3A and 3B illustrate a device according to an exemplary embodiment of the present disclosure including strip packaging for pen needles or syringe needles.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Exemplary embodiments of the present disclosure provide.

As would be readily appreciated by skilled artisans in the relevant art that, while descriptive terms such as "device" "pen needle", "syringe needle", "peel off", "cover", "hub" "seal," "inner", "outer", "shield", "strip", and others are used throughout this specification to facilitate understanding, it is not intended to limit any components that can be used in combinations or individually to implement various aspects of the embodiments of the present disclosure.

Referring now to the drawings, wherein like reference numerals designate identical or corresponding parts throughout the several views, embodiments of the present disclosure are described as follows.

Figure 3B:
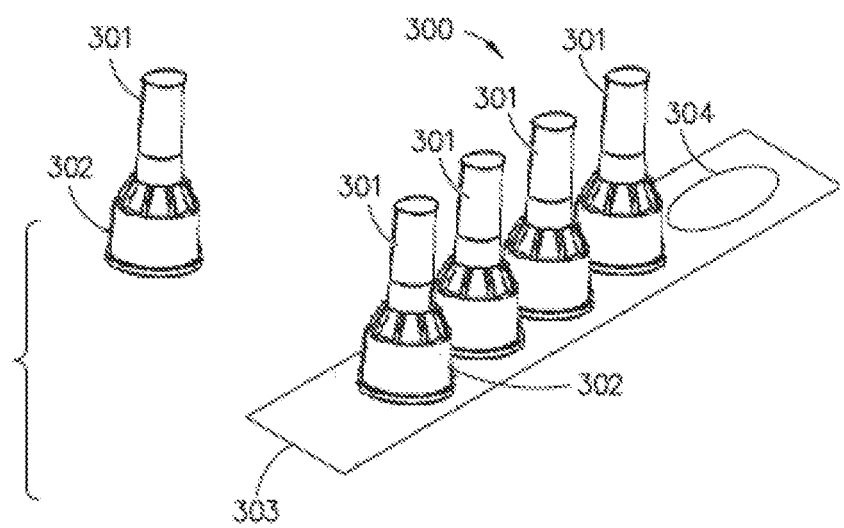

Referring to FIGS. 3A and 3B, a dispensing device 300 according to an exemplary embodiment of the present disclosure, includes a plurality of needle devices, such as pen needles 301 each provided with an outer cover 302, which covers the hub, needle and inner shield of a pen needle. Outer cover 302 includes an opening through which needle device can be exposed for use with an injection device. Strip 303 can optionally include an opening 304, for example for hanging strip 303 on an IV pole. Plurality of needle devices 301 are disposed on strip 303 such that strip 303 serves as a common seal for outer covers 302 of multiple pen needles 301 disposed on the strip 303. When outer cover 302 or a pen needle 301 is removed, or peeled off, from strip 303, the non-patient needle end of the huh of pen needle 301 is exposed and pen needle 310 is ready for immediate use.

Figure 4A:
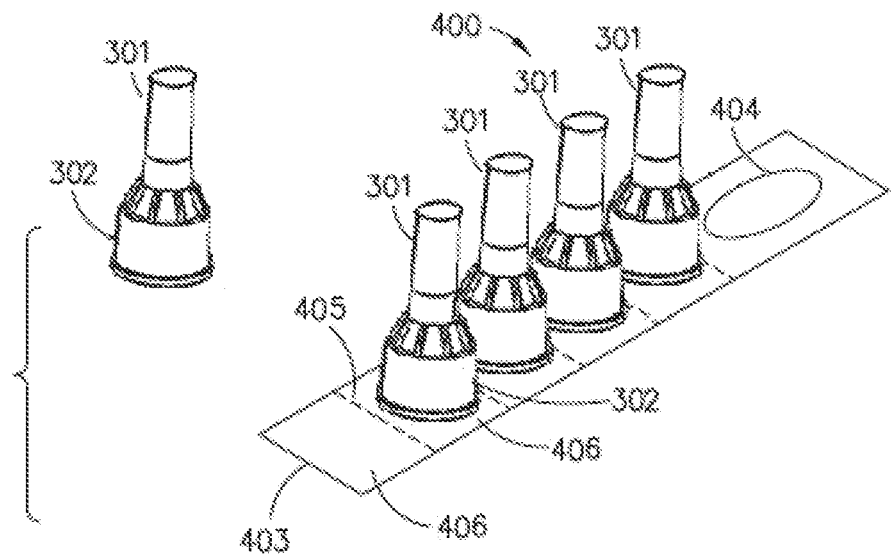
FIGS. 4A and 4B illustrate a device according to another exemplary embodiment of the present disclosure including strip packaging for pen needles or syringe needles.
Figure 4B:
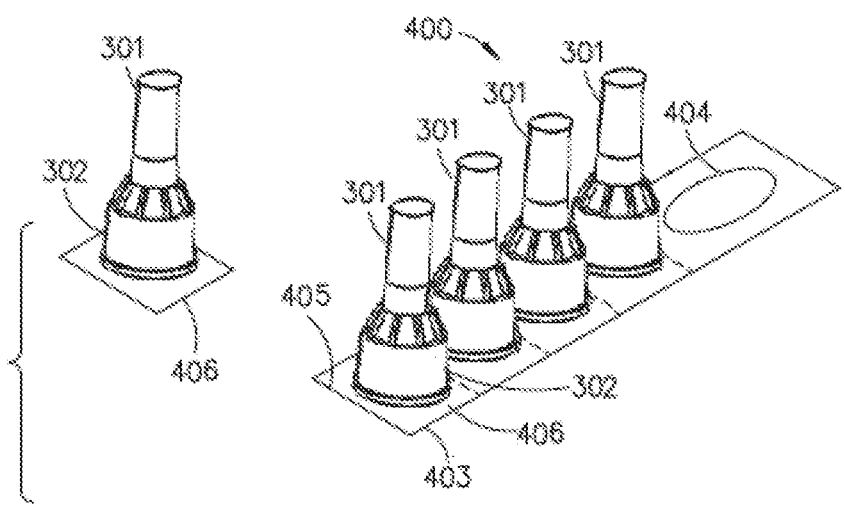

Referring to FIGS. 4A and 4B, a dispensing device 400 according to an exemplary embodiment of the present disclosure, includes a plurality of pen needles 301 disposed on a perforated strip 403. In an exemplary implementation, perforations 405 are firmed between pen needles 301 disposed on strip 403 to define portions 406 of strip 403 having at least one pen needles 301 disposed thereon. Pen needles 301 can be configured structurally and functionally like pen needles 301 illustrated in the examples of FIGS. 1A, 1B, 3A, and 3B and described above with reference thereto. In an exemplary implementation, strip 403 can be a peel strip configured as a cover attached to bottom outer cover 302 of each pen needle 301 to seal inner cavity of each cover 302, for example as described above with reference to FIGS. 1A, 1B, 3A and 3B. Strip 403 can optionally include an opening 404, for example for hanging strip 403 on an hanger, such as an IV pole.

As illustrated in the example of FIG. 4A, each pen needle 301 can be peeled off or separated from strip 403 for immediate use, for example, for attachment to an injection device. On the other hand, as illustrated in the example of FIG. 4B, portion 406 including a pen needle 301 disposed thereon can be selectively separated from strip 403 at perforation 405 such that inner cavity of cover 302 remains sealed by the portion 406 similar to individual pen needle 10 illustrated in the example of FIG. 1A.

Figure 5:
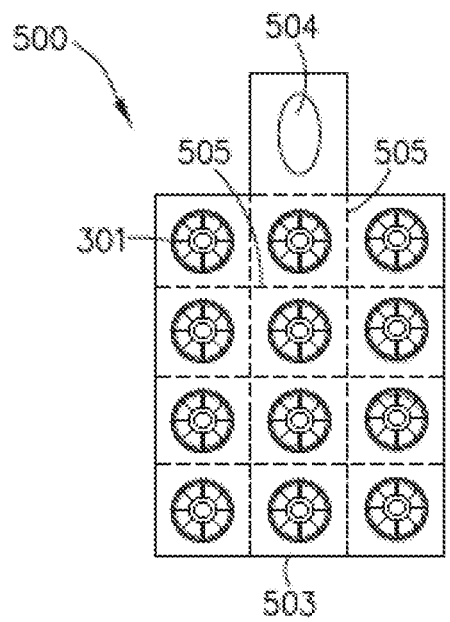
FIG. 5 illustrates a device according to yet another exemplary embodiment of the present disclosure including strip packaging for pen needles or syringe needles.

According to an exemplary implementation of exemplary embodiments of the present disclosure, dispensing device 500 can be configured to have a perforated strip 503 having multiple rows of pen needles 301 separated by perforations 505, as illustrated in the example of FIG. 5 showing a top view of such an implementation. According to another exemplary implementation, dispensing device 500 can be configured to have multiple rows, or any other arrangement, of pen needles 301 without perforations 505, or having one or more perforations separating individual or groups of pen needles 301 disposed m strip 503. Strip 503 can optionally include an opening 504, for example for hanging strip 503 on a hanger.

Figure 6:
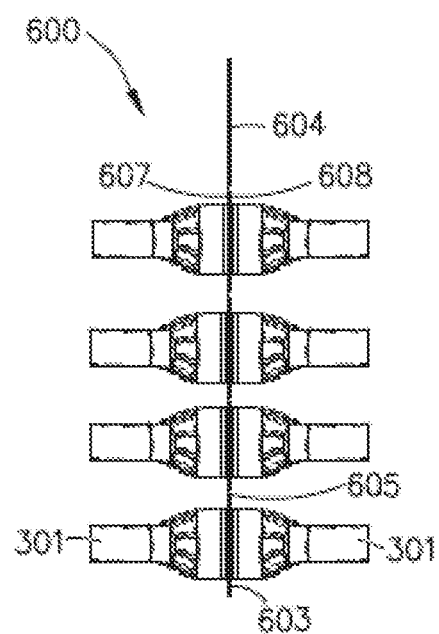
FIG. 6 illustrates a device according to a further exemplary embodiment of the present disclosure including strip packaging for pen needles or syringe needles.

According to yet another exemplary implementation as illustrated in a side view of FIG. 6 , dispensing device 600 can be configured to have a double-sided perforated peel strip 603 having two opposing sides 607 and 608, and pen needles 301 attached at both sides thereof. Peel strip 603 can be optionally provided with one or more perforations 605 such that two sealed pen needles 301 can be selectively detached from strip 603 at perforation 605 for later use. Pen needles 301 can be individually removed from either side of strip 603 for immediate use. Strip 603 can optionally include an opening 604, for example for hanging strip 603 on a hanger.

As illustrated in FIGS. 4A, 4B, 5, and 6, strip 400, 500, 600 is essentially flat and can have perforations in-between each pen needle 301, or groups/sets of pen needles 301. Hence a perforated strip section can be torn off or detached from, the main strip such that the pen needles 301 can be peeled opened for later use. Or, alternatively each pen needle 301 can be peeled open from the strip for immediate use.

In exemplary implementations, strip 303/403/503/603 includes an attachment portion, such as an opening 304/404/504/604 at least at one end thereof, for example to accommodate a hanger such that device 300/400/400/600 can be hung on, for example an IV pole for convenience. Other variations of an attachment portion, or means for selectively placing or hanging strip 303/403/503/603, such as a hook or the like, can be integral with, or attached to, strip 303/403/503/603 as would be readily appreciated by one of ordinary skill in the art.

In further exemplary implementations, strip 303/403/503/603 can comprise, or consist of a foil sheet that acts as a sterility barrier. In yet further exemplary implementation layered polypropylene can be used to melt onto the pen needle or syringe needle plastics and provide a non-permeable seal.

While the present disclosure has been shown and described with reference to certain exemplary embodiments thereof, it will be understood by those skilled in the art that various changes in form and details may be made therein without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of disclosure.

Other objects, advantages and salient features of the disclosure will become apparent to those skilled in the art from the details provided, which, taken in conjunction with the annexed drawing figures, disclose exemplary embodiments of the disclosure.

The invention claimed is:

1. A system for storing and dispensing needles, the system comprising: a first plurality of needle devices and a second plurality of needle devices, each of said needle devices including a needle and an outer cover covering said needle; and a strip attached to said outer cover of said each of said needle devices, said strip providing a corner seal for said outer cover of said each of said needle devices, wherein each of said needle devices is configured to be individually removable from said strip, and removal of said needle device from said strip detaches said strip from said outer cover of said removed needle device and exposes said needle of said removed needle device for immediate use; and wherein the first plurality of needle devices are sealingly attached to a first side of said strip and the second plurality of needle devices are sealingly attached to a second side of said strip opposite to the first side of said strip, wherein the strip defines a common plane between the first plurality of needle devices and the second plurality of needle devices.

2. The system of claim 1, wherein said strip comprises a plurality of portions separated by at least one perforation between said portions.

3. The system of claim 2, comprising at least two needle devices, wherein one of said needle devices is attached to one of said portions of said strip, and another of said needle devices is attached to another of said portions of said strip separated from said one portion by said perforation.

4. The system of claim 3, wherein at least one of said at least two needle devices is detachable from said strip at said perforation.

5. The system of claim 4, wherein when said at least one of said at least two needle devices is detached from said strip, said one portion of said strip is detached from said strip at said perforation, and said at least one of said at least two needle devices remains attached to said one portion of said strip.

6. The system of claim 2, wherein said strip comprises a plurality of rows of said needle devices disposed thereon, each of said needle devices having said outer cover sealingly attached to said strip.

7. The system of claim 6, wherein said strip comprises a plurality of perforations defining a plurality of portions of said strip detachable from said strip via one or more of said separations.

8. The system of claim 7, wherein each of said portions comprises one or more of said plurality of needle devices sealingly attached to said portions.

9. The system of claim 1, wherein said strip comprises an attachment for disposing said strip on a hanger.

10. The system of claim 1, wherein at least first and second of said needle devices are sealingly attached to said first side, and at least third and fourth of said needle devices are sealingly attached to said second side.

11. The system of claim 10, wherein said strip further comprises at least one perforation separating said strip into at least first and second portions.

12. The system of claim 11, wherein each of said first and second portions comprises said first side and said second side.

13. The system of claim 12, wherein said first needle device is sealing disposed on said first side of said first portion, said second needle device is sealing disposed on said second side of said first portion, said third needle device is sealing disposed on said first side of said second portion, and said fourth needle device is sealing disposed on said second side of said second portion.

14. The system of claim 11, wherein said first portion is detachable from said second portion via said perforation.

15. The system of claim 10, wherein one of said first and second needle devices is removable from said strip for immediate use without removing an other of said first and second needle devices from said strip.

16. The system of claim 1, further comprising a hook that is integral with or attached to said strip.

17. The system of claim 1, wherein the strip comprises a layer of polypropylene that forms a non-permeable seal with each of the plurality of needle devices.

18. The system of claim 1, wherein each of the first plurality of needle devices is longitudinally aligned with a corresponding one of the second plurality of needle devices.

19. The system of claim 1, wherein each of the first plurality of needle devices and the second plurality of needle devices are in symmetrical arrangement about the common plane defined by the strip.

* * * * *